United States Patent
Casey et al.

(10) Patent No.: US 10,947,473 B2
(45) Date of Patent: Mar. 16, 2021

(54) LESS CORROSIVE ORGANIC COMPOUNDS AS LUBRICANT ADDITIVES

(71) Applicant: VANDERBILT CHEMICALS, LLC, Norwalk, CT (US)

(72) Inventors: Brian M. Casey, Norwalk, CT (US); Vincent J. Gatto, Bradenton, FL (US)

(73) Assignee: VANDERBILT CHEMICALS, LLC, Norwalk, CT (US)

( * ) Notice: Subject to any disclaimer, the term of this patent is extended or adjusted under 35 U.S.C. 154(b) by 0 days.

(21) Appl. No.: 16/415,535

(22) Filed: May 17, 2019

(65) Prior Publication Data

US 2020/0362261 A1    Nov. 19, 2020

(51) Int. Cl.
| | |
|---|---|
| *C10M 133/16* | (2006.01) |
| *C07C 233/38* | (2006.01) |
| *C07C 231/02* | (2006.01) |
| *C10N 30/06* | (2006.01) |
| *C10N 30/12* | (2006.01) |
| *C10N 40/25* | (2006.01) |

(52) U.S. Cl.
CPC ......... *C10M 133/16* (2013.01); *C07C 231/02* (2013.01); *C07C 233/38* (2013.01); *C10M 2215/28* (2013.01); *C10N 2030/06* (2013.01); *C10N 2030/12* (2013.01); *C10N 2040/252* (2020.05); *C10N 2040/255* (2020.05)

(58) Field of Classification Search
CPC ............. C10M 133/16; C10M 2215/28; C07C 233/38; C07C 231/02; C10N 2030/06; C10N 2040/252; C10N 2040/255; C10N 2030/12
See application file for complete search history.

(56) References Cited

U.S. PATENT DOCUMENTS

| | | |
|---|---|---|
| 2,992,994 A | 7/1961 | Albrecht et al. |
| 5,397,486 A | 3/1995 | Small |
| 5,560,853 A | 10/1996 | Chiu |
| 5,641,480 A | 6/1997 | Vermeer |
| 5,672,727 A | 9/1997 | Chiu |
| 6,531,443 B2 | 3/2003 | Perella |
| 9,321,976 B1 | 4/2016 | Fang et al. |
| 9,464,252 B2 | 10/2016 | Schwab et al. |
| 9,562,207 B2 | 2/2017 | Deblase et al. |
| 2018/0334635 A1 | 11/2018 | Ruhe, Jr. et al. |

FOREIGN PATENT DOCUMENTS

| | | | |
|---|---|---|---|
| DE | 10 61 966 B | 7/1959 | |
| DE | 1061966 B | * 7/1959 | ............... A61Q 5/02 |
| EP | 2 295 438 B1 | 3/2015 | |
| WO | 2016/189328 A1 | 12/2016 | |

OTHER PUBLICATIONS

Shigeharu Nagano, "Cosmetic from Human Placenta". Abstract of JP35012097, Aug. 27, 1960.
International Search Report dated Jun. 15, 2020, dated Jul. 2, 2020, in connection with International Application No. PCT/US2020/026350.

\* cited by examiner

*Primary Examiner* — Taiwo Oladapo
(74) *Attorney, Agent, or Firm* — Norris McLaughlin, P.A.

(57) ABSTRACT

A composition of matter represented by the following formula:

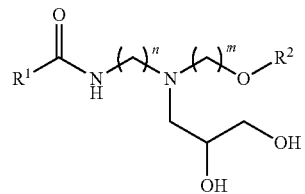

where $R^1$ is an unsaturated or branched hydrocarbon chain, $R^2$ is either a hydrogen atom or a hydrocarbon chain, and m and n are independently from 1 to 5, when used in a lubricating composition, being effective for friction and wear reduction, while providing improved protection against copper and lead corrosion in an engine.

8 Claims, No Drawings

LESS CORROSIVE ORGANIC COMPOUNDS AS LUBRICANT ADDITIVES

BACKGROUND OF THE INVENTION

Field of the Invention

This invention involves the development of less corrosive, high performing organic compounds with applications as additives in lubricants. Lubricants containing these compounds have demonstrated improved performance with respect to friction reduction, wear protection, and copper and lead corrosion. In particular, the compounds of the invention are N-[3-[(2,3-dihydroxypropyl)(3-alkoxypropyl)amino]propyl]alkylamides, and unsaturated or branched N-[2-[(2,3-dihydroxypropyl) (2-hydroxyethyl)amino]ethyl]-alkylamides.

The claimed compounds represent a new class of additives capable of meeting or exceeding the frictional and wear performance of traditional additives while significantly reducing the severity of the observed copper and lead corrosion. This inventive class of compounds is particularly useful in both passenger car motor oil and heavy-duty diesel engine oil applications where high performing, more durable friction modifier and/or anti-wear additives are required in terms of oxidative and hydrolytic stability.

Discussion of the Prior Art

In the prior art, DE1061966 and JP35012097 generally relate to this class of compounds. However, neither unsaturated nor branched examples of N-[2-[(2,3-dihydroxy-propyl)(2-hydroxyethyl)amino]ethyl]-alkylamides are contemplated; nor is there a discussion of N-[3-[(2,3-dihydroxypropyl)(3-alkoxypropyl)amino]propyl] alkylamides. Furthermore, neither DE1061966 nor JP35012097 contemplated use of this class of compounds in lubricants as additives for friction modification or wear protection.

DE 1061966 describes preparation of related 2,3-dihydroxy compounds by reacting intermediate alkylamide, N-[2-[(2-hydroxyethyl)amino]ethyl]-with α-chlorohydrin or epichlorohydrin. This process can require the use of caustic bases and generates halogenated waste. In the invention presented herein, intermediate alkylamide amines were reacted instead with glycidol in the presence of ethanol. These reactions benefit from being completely atom economical and generate no waste. The ethanol can be separated from the reaction by simple distillation and recycled into the process.

U.S. Pat. No. 5,397,486 teaches a reaction in which the glycidol adducts differ from those used in the reaction to form the inventive compounds. This reference uses glycidol adducts where X is oxygen, sulfur, or nitrogen and R is a hydrocarbyl radical containing 4-50 carbon atoms, the following formula

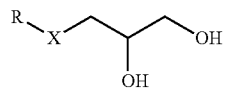

The inventive class of compounds are chemically distinct and outside the class described in U.S. Pat. No. 5,397,486. In addition, U.S. Pat. No. 5,397,486 describes lubricant compositions containing the above class of compounds as silver wear inhibiting additives specifically for applications in diesel engines having silver-surfaced engine parts. U.S. Pat. No. 9,464,252 teaches glycidol adducts but does not contemplate their role in terms of friction modifier performance, general wear protection, or impact on copper and lead corrosion.

U.S. Pat. Nos. 5,560,853, 5,672,727, 9,321,976, 9,464,252 teach reactions in which the glycidol adducts differ from those used in the reaction to form the inventive compounds. The inventive class of compounds are chemically distinct and outside the class described in these patents.

SUMMARY OF THE INVENTION

The class of compounds in the present invention may be represented in Formula I:

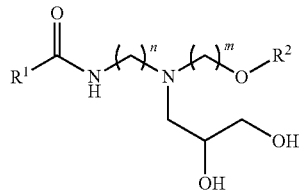

where $R^1$ is a hydrocarbon chain and $R^2$ is either a hydrogen atom or a hydrocarbon chain. The $R^1$ group consists of an unsaturated, and/or saturated, and/or linear and/or branched hydrocarbon chain containing 1 to 21 carbon atoms. It is preferred that the $R^1$ group is unsaturated or branched. It is further preferred that the $R^1$ group is both saturated and branched. It is also preferred that the $R^1$ group consists of a hydrocarbon chain containing 11 to 21 carbon atoms. The $R^2$ group can be a hydrogen atom or a linear, cyclic, or branched hydrocarbon chain containing 1 to 20 carbon atoms. The number of methylene spacer groups (n and m) are each independently from 1 to 5. It is preferred that the number of methylene spacer groups (n and m) are each independently 2 or 3.

This class of compounds can be prepared via General Reaction Scheme I:

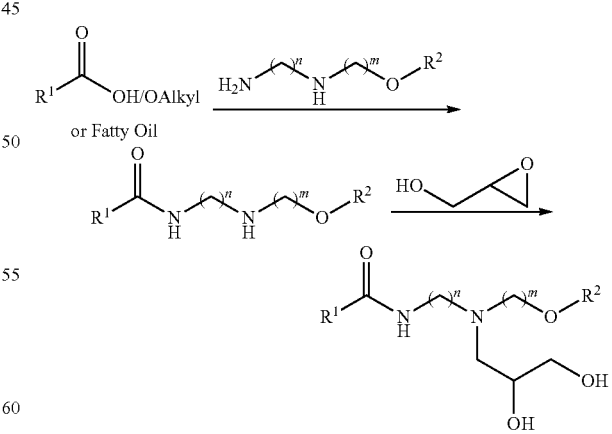

In the first step, a carbonyl-containing compound such as a carboxylic acid, carboxylic acid ester, or triglyceride is reacted with a mixed primary/secondary amine-containing compound to form a secondary amide. In the second step, the secondary amide intermediate is reacted further with glycidol to furnish the final product described in Formula I. The second step can be performed in the presence of a protic solvent such as methanol or ethanol to improve the reaction efficiency.

As highlighted above, the class of compounds in this invention may also be described as the reaction products of (a) a carboxylic acid or ester or triglyceride, (b) a mixed primary/secondary amine-containing compound, and (c) glycidol. Non-limiting examples of the compounds of this invention include the following:

N-[2-[(2,3-dihydroxypropyl)(2-hydroxyethyl)amino]ethyl]lauramide
N-[2-[(2,3-dihydroxypropyl)(2-hydroxyethyl)amino]ethyl]myristamide
N-[2-[(2,3-dihydroxypropyl)(2-hydroxyethyl)amino]ethyl]palmitamide
N-[2-[(2,3-dihydroxypropyl)(2-hydroxyethyl)amino]ethyl]stearamide
N-[2-[(2,3-dihydroxypropyl)(2-hydroxyethyl)amino]ethyl]isostearamide
N-[2-[(2,3-dihydroxypropyl)(2-hydroxyethyl)amino]ethyl]myristoleamide
N-[2-[(2,3-dihydroxypropyl)(2-hydroxyethyl)amino]ethyl]palmitoleamide
N-[2-[(2,3-dihydroxypropyl)(2-hydroxyethyl)amino]ethyl]oleamide
N-[2-[(2,3-dihydroxypropyl)(2-hydroxyethyl)amino]ethyl]linoleamide
N-[3-[(2,3-dihydroxypropyl)(3-isotridecyloxypropyl)amino]propyl]lauramide
N-[3-[(2,3-dihydroxypropyl)(3-isotridecyloxypropyl)amino]propyl]myristamide
N-[3-[(2,3-dihydroxypropyl)(3-isotridecyloxypropyl)amino]propyl]palmitamide
N-[3-[(2,3-dihydroxypropyl)(3-isotridecyloxypropyl)amino]propyl]stearamide
N-[3-[(2,3-dihydroxypropyl)(3-isotridecyloxypropyl)amino]propyl]isostearamide
N-[3-[(2,3-dihydroxypropyl)(3-isotridecyloxypropyl)amino]propyl]myristoleamide
N-[3-[(2,3-dihydroxypropyl)(3-isotridecyloxypropyl)amino]propyl]palmitoleamide
N-[3-[(2,3-dihydroxypropyl)(3-isotridecyloxypropyl)amino]propyl]oleamide
N-[3-[(2,3-dihydroxypropyl)(3-isotridecyloxypropyl)amino]propyl]linoleamide
N-[3-[(2,3-dihydroxypropyl)(3-butyloxypropyl)amino]propyl]lauramide
N-[3-[(2,3-dihydroxypropyl)(3-butyloxypropyl)amino]propyl]myristamide
N-[3-[(2,3-dihydroxypropyl)(3-butyloxypropyl)amino]propyl]palmitamide
N-[3-[(2,3-dihydroxypropyl)(3-butyloxypropyl)amino]propyl]stearamide
N-[3-[(2,3-dihydroxypropyl)(3-butyloxypropyl)amino]propyl]isostearamide
N-[3-[(2,3-dihydroxypropyl)(3-butyloxypropyl)amino]propyl]myristoleamide
N-[3-[(2,3-dihydroxypropyl)(3-butyloxypropyl)amino]propyl]palmitoleamide
N-[3-[(2,3-dihydroxypropyl)(3-butyloxypropyl)amino]propyl]oleamide
N-[3-[(2,3-dihydroxypropyl)(3-butyloxypropyl)amino]propyl]linoleamide
N-[3-[(2,3-dihydroxypropyl)(3-octyloxypropyl)amino]propyl]lauramide
N-[3-[(2,3-dihydroxypropyl)(3-octyloxypropyl)amino]propyl]myristamide
N-[3-[(2,3-dihydroxypropyl)(3-octyloxypropyl)amino]propyl]palmitamide
N-[3-[(2,3-dihydroxypropyl)(3-octyloxypropyl)amino]propyl]stearamide
N-[3-[(2,3-dihydroxypropyl)(3-octyloxypropyl)amino]propyl]isostearamide
N-[3-[(2,3-dihydroxypropyl)(3-octyloxypropyl)amino]propyl]myristoleamide
N-[3-[(2,3-dihydroxypropyl)(3-octyloxypropyl)amino]propyl]palmitoleamide
N-[3-[(2,3-dihydroxypropyl)(3-octyloxypropyl)amino]propyl]oleamide
N-[3-[(2,3-dihydroxypropyl)(3-octyloxypropyl)amino]propyl]linoleamide
N-[3-[(2,3-dihydroxypropyl)(3-decyloxypropyl)amino]propyl]lauramide
N-[3-[(2,3-dihydroxypropyl)(3-decyloxypropyl)amino]propyl]myristamide
N-[3-[(2,3-dihydroxypropyl)(3-decyloxypropyl)amino]propyl]palmitamide
N-[3-[(2,3-dihydroxypropyl)(3-decyloxypropyl)amino]propyl]stearamide
N-[3-[(2,3-dihydroxypropyl)(3-decyloxypropyl)amino]propyl]isostearamide
N-[3-[(2,3-dihydroxypropyl)(3-decyloxypropyl)amino]propyl]myristoleamide
N-[3-[(2,3-dihydroxypropyl)(3-decyloxypropyl)amino]propyl]palmitoleamide
N-[3-[(2,3-dihydroxypropyl)(3-decyloxypropyl)amino]propyl]oleamide
N-[3-[(2,3-dihydroxypropyl)(3-decyloxypropyl)amino]propyl]linoleamide
N-[2-[(2,3-dihydroxypropyl)(3-decyloxypropyl)amino]ethyl]oleamide
N-[3-[(2,3-dihydroxypropyl)(2-decyloxyethyl)amino]propyl]oleamide
N-[2-[(2,3-dihydroxypropyl)(3-hydroxypropyl)amino]ethyl]oleamide
N-[3-[(2,3-dihydroxypropyl)(2-hydroxyethyl)amino]propyl]oleamide
N-[2-[(2,3-dihydroxypropyl)(3-decyloxypropyl)amino]ethyl]isostearamide
N-[3-[(2,3-dihydroxypropyl)(2-decyloxyethyl)amino]propyl]isostearamide
N-[2-[(2,3-dihydroxypropyl)(3-hydroxypropyl)amino]ethyl]isostearamide
N-[3-[(2,3-dihydroxypropyl)(2-hydroxyethyl)amino]propyl]isostearamide

DETAILED DESCRIPTION OF THE INVENTION

The following two-step procedure is a representative example for the preparation of the class of compounds described in the present invention: 664 mmol of oleic acid is added to a 3-neck flask fitted with a temperature probe, mechanical stirrer, and distillation trap fitted with a condenser. To the flask is added 664 mmol of 2-aminoethylethanolamine and the reaction is placed under a nitrogen atmosphere. The reaction is heated to 150° C. and the generated water is collected in the distillation trap. After heating for approximately 6 hrs, the reaction is cooled and the product amide is used directly in the next step without purification.

271 mmol of the product from the previous step is added to a 3-neck flask fitted with a temperature probe and mechanical stirrer. 275 mL of ethanol is added to the flask and a reflux condenser is attached. A solution consisting of 258 mmol of glycidol in 70 mL of ethanol is prepared and transferred to an addition funnel with a nitrogen inlet attached atop the reflux condenser. The reaction is placed under nitrogen atmosphere and heated to reflux (approximately 80° C.). The solution of glycidol is added dropwise to the flask over 30 min. After the addition is complete, the reaction is refluxed for an additional 6 hrs. The reaction was concentrated via rotary evaporation until all the ethanol is removed to yield the desired product.

In carrying out the above reactions, a variety of starting materials may be used as depicted in General Reaction Scheme I. In the first step, the carbonyl-containing compound such as a carboxylic acid, carboxylic acid ester, or triglyceride may be used. For carboxylic acids, the $R^1$ group consisting of 1 to 21 carbon atoms can be a linear, cyclic, or branched saturated hydrocarbon or an unsaturated and/or polyunsaturated hydrocarbon or mixtures thereof. For carboxylic acid esters, the $R^1$ group consisting of 1 to 21 carbon atoms can be a linear, cyclic, or branched saturated hydrocarbon or an unsaturated and/or polyunsaturated hydrocarbon or mixtures thereof. For triglycerides, the $R^1$ group consisting of 1 to 21 carbon atoms can be a linear, cyclic, or branched saturated hydrocarbon or an unsaturated and/or polyunsaturated hydrocarbon or mixtures thereof. For the reaction of a carboxylic acid or carboxylic acid ester with the primary amine-containing compound, the reaction stoichiometry is typically 1.0 mole of carboxylic acid or carboxylic acid ester to 1.0 mole of the primary amine-containing compound to produce the desired secondary amide. Slight excesses or the carboxylic acid or carboxylic acid ester, or the primary amine-containing compound may be used but are generally not necessary nor preferred. Preferred carboxylic acid esters are fatty acid methyl esters (FAME's) and fatty acid ethyl esters, also referred to as biodiesel. Sources of biodiesel are the fatty oils described below. For the reaction of a triglyceride with the primary amine-containing compound, the reaction stoichiometry can be varied such that 1.0 mole of triglyceride is reacted with 1.0 to 3.0 mole of the primary amine-containing compound to produce the desired secondary amide and/or a mixture of the desired secondary amide with the corresponding mono- and dialkylglycerates. The carbon chains in the above examples of carbonyl-containing compounds can be derived from fatty oils such as coconut oil, hydrogenated coconut oil, fish oil, hydrogenated fish oil, tallow, hydrogenated tallow, corn oil, rapeseed oil, cottonseed oil, olive oil, palm oil, peanut oil, safflower oil, sesame oil, sunflower oil, canola oil, and soy bean oil. For the mixed primary/secondary amine-containing compound, the $R^2$ group can be a hydrogen atom or a linear, cyclic, or branched hydrocarbon chain containing 1 to 20 carbon atoms or mixtures thereof and the number of methylene spacer groups (n and m) can vary from 1 to 5.

The following examples were prepared using the representative procedure provided above:

Example 1 (Ex. 1)

The preparative procedure for N-[2-[(2,3-dihydroxypropyl)(2-hydroxyethyl)amino]-ethyl]oleamide was identical to the representative procedure.

Example 2 (Ex. 2)

The preparative procedure for N-[3-[(2,3-dihydroxypropyl)(3-isotridecyloxypropyl)amino]-propyl]oleamide was identical to the representative procedure except that isotridecyloxypropyl-1,3-diaminopropane was used in place of 2-aminoethylethanolamine.

Example 3 (Ex. 3)

The preparative procedure for N-[2-[(2,3-dihydroxypropyl)(2-hydroxyethyl)amino]ethyl]-cocoamide was identical to the representative procedure except that coconut oil methyl esters were used in place of oleic acid.

Example 4 (Ex. 4)

The preparative procedure for N-[3-[(2,3-dihydroxypropyl)(3-isotridecyloxypropyl)amino]-propyl]cocoamide was identical to the representative procedure except that coconut oil methyl esters were used in place of oleic acid and isotridecyloxypropyl-1,3-diaminopropane was used in place of 2-aminoethylethanolamine.

Example 5 (Ex. 5)

The preparative procedure for N-[2-[(2,3-dihydroxypropyl)(2-hydroxyethyl)amino]ethyl]isostearamide was identical to the representative procedure except that isostearic acid was used in place of oleic acid.

The following compounds are included as comparative examples to the invention disclosed herein:

Comparative Example 1 (CEx. 1)

Glycerol monooleate (HiTEC® 7133 from Afton Chemical)

Comparative Example 2 (Cex. 2)

A commercial organic friction modifier comprised of the products of the reaction of 1.0 mole of fatty oil having 12 or more carbon atoms and 1.0-2.5 moles of diethanolamine.

Individual compounds from the inventive class of molecules can be used as additives in lubricants for friction reduction and/or supplemental wear protection at a treat rate from about 0.01-5.00 wt. %, preferably about 0.10-3.00%, and more preferably about 0.20-2.00%, and still more preferably about 0.40-1.00%, as weight percentage of the overall lubricating composition. Furthermore, these compounds can be used in combination with other additives such as dispersants, detergents, viscosity modifiers, antioxidants, other friction modifiers, anti-wear agents, corrosion inhibitors, rust inhibitors, salts of fatty acids (soaps), and extreme pressure additives.

Dispersants that may be used include polyisobutylene mono-succinimide dispersants, polyisobutylene di-succinimide dispersants, polypropylene mono-succinimide dispersants, polypropylene di-succinimide dispersants, ethylene/propylene copolymer mono-succinimide dispersants, ethylene/propylene copolymer di-succinimide dispersants, Mannich dispersants, dispersant antioxidant olefin copolymers, low molecular weight ethylene propylene succimimide dispersants, carboxylic dispersants, amine dispersants, boronated dispersants, and molybdenum containing dispersants.

Detergents that may be used include neutral calcium sulfonate detergents, neutral magnesium sulfonate detergents, overbased calcium sulfonate detergents, overbased magnesium sulfonate detergents, neutral calcium phenate detergents, neutral magnesium phenate detergents, overbased calcium phenate detergents, overbased magnesium phenate detergents, neutral calcium salicylate detergents, neutral magnesium salicylate detergents, overbased calcium salicylate detergents, overbased magnesium salicylate detergents, sodium sulfonate detergents, and lithium sulfonate detergents.

Any type of polymeric viscosity index modifier may be used. Examples include polymers based on olefin copolymers (OCPs), polyalkylmethacrylates (PAMAs), polyisobutylenes (PIBs), styrene block polymers (such as styrene isoprene, styrene butadiene), and ethylene alpha-olefin copolymers.

Molybdenum-based friction modifiers may be used to supplement or enhance the overall performance of the class of compounds in this invention. Examples of the types of alternative friction modifiers that may be used include molybdenum complexes prepared by reacting a fatty oil, diethanolamine and a molybdenum source, molybdate esters, mononuclear molybdenum dithiocarbamates, dinuclear molybdenum dithiocarbamates, trinuclear molybdenum dithiocarbamates, sulfurized oxymolybdenum dithiocarbamates, sulfur and molybdenum containing compounds, amine and molybdenum containing compounds, molybdenum phosphorodithioates, sulfurized oxymolybdenum dithiophosphates, tetraalkylammonium thiomolybdates, molybdenum carboxylates, molybdenum xanthates, molybdenum thioxanthates, imidazolium oxythiomolybdate salts, and quaternary ammonium oxythiomolybdate salts. Typical treat rates for molybdenum-based friction modifiers range from 50 ppm to 800 ppm of delivered molybdenum to the finished lubricant formulation.

It is preferred that additives such as glycerol monooleate and organic friction modifiers derived from fatty oils and diethanolamine are not present because, as will be demonstrated, these types of organic friction modifiers are highly corrosive to copper and lead as determined by the high temperature corrosion bench test (HTCBT, ASTM D6594). Accordingly, the invention also comprises lubricating composition which are free of glycerol monooleate and organic friction modifiers derived from fatty oils and diethanolamine.

Preferred anti-wear additives that may be used include primary and/or secondary zinc dialkyldithiophosphate (ZDDP), triphenylphosphorothioates, dialkylphosphoric acid amine salts, monoalkylphosphoric acid amine salts, dialkyldithiophosphate succinates, dithiophosphoric ester or carboxylic acids, trialkylborate esters, borate esters of fatty acid derivatives, and methylenebis(dibutyldithiocarbamate).

Preferred antioxidants that may be used include dinonyldiphenylamine, mononyldiphenylamine, dioctyldiphenylamine, monooctyldiphenylamine, butyloctyldiphenylamine, monobutyldiphenylamine, dibutyldiphenylamine, nonylated phenyl-alpha-naphthylamine octylated phenyl-alpha-naphthylamine, dodecylated phenyl-alpha-naphthylamine, 2,6-di-tert-butylphenol, butylated hydroxytoluene, 4,4-methylenebis(2,6-di-tert-butylphenol), octadecyl-3-[3,5-di-tert-butyl-4-hydroxyphenyl]propionate, isotridecyl-3-[3,5-di-tert-butyl-4-hydroxyphenyl]propionate, 2-ethylhexyl-3-[3,5-di-tert-butyl-4-hydroxyphenyl]propionate, isooctyl-3-[3,5-di-tert-butyl-4-hydroxyphenyl]propionate and thiodiethylene bis [3-(3,5-di-tert-butyl-4-hydroxyphenyl) propionate].

Preferred corrosion and rust inhibitors that may be used include ethoxylated phenols, alkenylsuccinic acids, polyalkylene glycols, derivatives of benzotriazole, derivatives of tolutriazole, derivatives of triazole, dimercaptothiadiazole derivatives, fatty acid derivatives of 4,5-dihydro-1H-imidazole, neutral calcium dinonylnaphthalene sulfonates, neutral zinc dinonylnaphthalene sulfonates, and neutral alkaline earth sulfonates.

Preferred extreme pressure additives that may be used include sulfurized isobutylene, sulfurized alpha-olefins, aliphatic amine phosphates, aromatic amine phosphates, dimercaptothiadiazole derivatives, zinc dialkyldithiocarbamates, dialkylammonium dialkyldithiocarbamates, and antimony dialkyldithiocarbamates.

Treat levels for all the above-mentioned additives can vary significantly depending upon the application, additive solubility, base fluid type, and finished fluid performance requirements. Typical treat levels usually vary from 0.05 wt. % to 10.00 wt. % based on the type of finished lubricant being developed. Base fluids may include petroleum-based or synthetic stocks including any fluid that falls into the API base stock classification as Group I, Group II, Group III, Group IV, and Group V. Synthetic fluids include poly-α-olefins, polyols, esters, bio-based lubricants, and any combination of these. A lubricating base oil is present in an amount of at least 80% of a total lubricating composition.

The results of performance evaluations for the inventive examples and the comparative examples are described in Examples 6-9. In Examples 6-8, inventive and comparative examples were blended into an SAE 0W-20 passenger car motor oil (0W-20 PCMO) at treat rates of 0.40-1.00 weight percent. This oil was fully formulated except that it excluded an organic or organometallic friction modifier (FM). In Example 9, inventive and comparative examples were blended into a commercial, CK-4 equivalent SAE 15W-40 heavy duty diesel engine oil (15W-40 HDDEO) at a treat rate of 0.75 weight percent.

Example 6

Tribological Performance Testing by SRV

The test method described for ASTM D5707 (Standard Test Method for Measuring Friction and Wear Properties of Lubricating Grease Using a High-Frequency, Linear-Oscillation (SRV) Test Machine) was followed to generate the performance data contained in Table 1. The results presented in Table 1 clearly indicate that both the inventive and comparative examples provided additional wear protection as evidenced by lower wear volumes compared to the 0W-20 PCMO reference oil containing no FM. The improvements from the inventive examples provided between 40-56% reductions in the wear volume. In addition, inventive Ex. 2 and Ex. 4 provided a modest improvement in the average coefficients of friction compared to the 0W-20 PCMO reference oil.

TABLE 1

Tribological Performance Testing by SRV (ASTM D5707)

| Additive | FM Treat Rate (wt. %) | Wear Volume ($\mu m^3$) | Average Coefficient of Friction |
|---|---|---|---|
| 0W-20 PCMO | 0 | 54,055 | 0.144 |
| +CEx. 1 | 0.80 | 41,699 | 0.132 |
| +CEx. 2 | 0.80 | 15,145 | 0.140 |
| +Ex. 1 | 0.80 | 32,387 | 0.144 |
| +Ex. 2 | 0.80 | 23,690 | 0.137 |
| +Ex. 3 | 0.80 | 24,121 | 0.152 |
| +Ex. 4 | 0.80 | 26,987 | 0.138 |

Example 7

Tribological Performance Testing by Four-Ball Wear

The test method described for ASTM D4172 B (Standard Test Method for Wear Preventive Characteristics of Lubricating Fluid (Four-Ball Method) was followed to generate the performance data contained in Table 2. Under these test conditions, all four inventive examples provided lower average coefficients of friction compared to the 0W-20 PCMO reference oil containing no FM. In addition, Ex. 2 and Ex. 4 provided improved wear protection as indicated by reductions in the wear scar diameter.

TABLE 2

Tribological Performance Testing by Four-Ball Wear (ASTM D4172 B)

| Additive | FM Treat Rate (wt. %) | Wear Scar Diameter (mm) | Average Coefficient of Friction |
|---|---|---|---|
| 0W-20 PCMO | 0 | 0.45 | 0.099 |
| +CEx. 1 | 0.80 | 0.34 | 0.062 |
| +CEx. 2 | 0.80 | 0.34 | 0.066 |
| +Ex. 1 | 0.80 | 0.43 | 0.094 |
| +Ex. 2 | 0.80 | 0.34 | 0.062 |
| +Ex. 3 | 0.80 | 0.45 | 0.086 |
| +Ex. 4 | 0.80 | 0.36 | 0.079 |

Example 8

Tribological Performance Testing by Mini Traction Machine (MTM)

Mini Traction Machine (MTM) was used to evaluate frictional characteristics of lubricants in boundary and mixed lubrication regime (Stribeck Curve) with "Ball on Disc" configuration. MTM consists of a rotating 52100 steel ball pressed against an independently rotating 52100 steel disc immersed in the lubricant. The operating conditions are set by independently controlling the rotational velocities of the shafts that drives the ball and the disc, in order to obtain a particular combination of rolling speed and slide to roll ratio, as well as by controlling the contact force and the oil bath temperature. The test method parameters used to generate the frictional performance data contained in Tables 3-6 from the Mini Traction Machine (MTM) are as follows: 35 N load (~1 GPa), 50% slide: roll ratio, speed run from 3000 mm/s to 10 mm/s, 52100 steel. For each formulation, three Stribeck curves were generated at 40° C., 60° C., 80° C., 100° C., 120° C., and 140° C. The average value from the three runs was reported at each temperature.

Table 3 demonstrates the improvements in the boundary coefficients of friction for the inventive examples compared to the 0W-20 PCMO reference oil containing no FM. In particular, once the temperature is at or above 80° C., all five inventive examples provided lower boundary coefficients. Most notably, inventive Ex. 1 had the lowest boundary coefficient of friction at temperatures of 60° C. and above for all of the additives evaluated. Table 4 contains the results for the Stribeck Coefficients obtained for the oils at each temperature. For temperatures at or above 100° C., all inventive examples significantly improved the frictional performance of the oil compared to the formulation containing no FM. Of note, both inventive Ex. 1 and 5 provided lower Stribeck Coefficients at temperatures at or above 60° C. than the reference oil without friction modifier and oils containing either comparative example. Similar to the frictional data in the boundary lubrication regime, the oil containing inventive Ex. 1 provided significantly lower Stribeck Coefficients than every other friction modifier additive evaluated at temperatures from 80-140° C. These results indicate that inventive Ex. 1 not only improves the frictional performance in the boundary lubrication regime but also into the mixed and elastohydrodynamic regimes.

TABLE 3

Tribological Performance Testing by MTM

| Additive | FM Treat Rate (wt. %) | Boundary Coefficient of Friction* at Specified Temperature | | | | | |
|---|---|---|---|---|---|---|---|
| | | 40° C. | 60° C. | 80° C. | 100° C. | 120° C. | 140° C. |
| 0W-20 PCMO | 0 | 0.076 | 0.094 | 0.113 | 0.128 | 0.127 | 0.128 |
| +CEx. 1 | 0.80 | 0.091 | 0.095 | 0.090 | 0.090 | 0.088 | 0.077 |
| +CEx. 2 | 0.80 | 0.102 | 0.107 | 0.110 | 0.104 | 0.103 | 0.105 |
| +Ex. 1 | 0.80 | 0.086 | 0.093 | 0.090 | 0.086 | 0.079 | 0.075 |
| +Ex. 2 | 0.80 | 0.089 | 0.098 | 0.100 | 0.097 | 0.098 | 0.098 |
| +Ex. 3 | 0.80 | 0.084 | 0.110 | 0.101 | 0.109 | 0.098 | 0.086 |
| +Ex. 4 | 0.80 | 0.092 | 0.103 | 0.106 | 0.100 | 0.096 | 0.093 |
| +Ex. 5 | 0.80 | 0.079 | 0.096 | 0.103 | 0.097 | 0.089 | 0.082 |

*Reported coefficients are the average of three runs. Boundary coefficient is the coefficient of friction at a speed of 10 mm/s.

TABLE 4

Tribological Performance Testing by MTM

| Additive | FM Treat Rate (wt. %) | Stribeck Coefficient* at Specified Temperature | | | | | |
|---|---|---|---|---|---|---|---|
| | | 40° C. | 60° C. | 80° C. | 100° C. | 120° C. | 140° C. |
| 0W-20 PCMO | 0 | 0.135 | 0.141 | 0.167 | 0.219 | 0.268 | 0.278 |
| +CEx. 1 | 0.80 | 0.142 | 0.156 | 0.168 | 0.180 | 0.191 | 0.181 |
| +CEx. 2 | 0.80 | 0.160 | 0.158 | 0.159 | 0.159 | 0.172 | 0.198 |
| +Ex. 1 | 0.80 | 0.145 | 0.138 | 0.133 | 0.134 | 0.134 | 0.138 |
| +Ex. 2 | 0.80 | 0.148 | 0.152 | 0.161 | 0.172 | 0.197 | 0.218 |
| +Ex. 3 | 0.80 | 0.141 | 0.169 | 0.176 | 0.196 | 0.201 | 0.196 |
| +Ex. 4 | 0.80 | 0.149 | 0.152 | 0.164 | 0.170 | 0.178 | 0.184 |
| +Ex. 5 | 0.80 | 0.134 | 0.135 | 0.140 | 0.144 | 0.157 | 0.163 |

*Stribeck coefficients are calculated by taking the integration of the Stribeck curve at each individual temperature.

Table 5 further demonstrates the improvements in the boundary coefficients of friction for the inventive examples compared to the 0W-20 PCMO reference oil that contains no friction modifier. In these studies, formulations containing either inventive or comparative examples at three different treat rates were evaluated. From the data provided in Table 5, at temperatures at or above 80° C. all three inventive examples provided lower boundary coefficients than the reference oil without any FM even at the lowest treat rate (0.40 wt. %). Table 6 contains the results for the Stribeck Coefficients obtained for the oils at each temperature and treat rate. Again, once operating temperatures were at or above 80° C., all three inventive examples at each treat rate demonstrated improved friction compared to the 0W-20 reference oil containing no FM as evidenced by lower Stribeck Coefficients. As with the data shown in Table 4 above, formulations containing inventive Ex. 1 demonstrated exceptional friction reduction especially at higher operating temperatures and treat rates. In particular, inventive Ex. 1 provided the lowest observed Stribeck Coefficients for any of the additives evaluated from 100-140° C. at the highest treat rate. These data in Tables 5 and 6 again indicate that inventive Ex. 1 not only improves the frictional performance in the boundary lubrication regime but also into the mixed and elastohydrodynamic regimes across a range of treat rates.

TABLE 5

Tribological Performance Testing by MTM at Additional Treat Rates

| Additive | FM Treat Rate (wt. %) | Boundary Coefficient of Friction* at Specified Temperature | | | | | |
|---|---|---|---|---|---|---|---|
| | | 40° C. | 60° C. | 80° C. | 100° C. | 120° C. | 140° C. |
| 0W-20 PCMO | 0 | 0.076 | 0.094 | 0.113 | 0.128 | 0.127 | 0.128 |
| +CEx. 1 | 0.40 | 0.078 | 0.086 | 0.085 | 0.077 | 0.074 | 0.064 |
| +CEx. 2 | 0.40 | 0.092 | 0.101 | 0.095 | 0.089 | 0.086 | 0.105 |
| +Ex. 1 | 0.40 | 0.091 | 0.096 | 0.098 | 0.092 | 0.085 | 0.080 |
| +Ex. 2 | 0.40 | 0.088 | 0.102 | 0.104 | 0.100 | 0.097 | 0.093 |
| +Ex. 5 | 0.40 | 0.088 | 0.104 | 0.111 | 0.108 | 0.100 | 0.089 |
| +CEx. 1 | 0.60 | 0.072 | 0.075 | 0.078 | 0.076 | 0.072 | 0.067 |
| +CEx. 2 | 0.60 | 0.094 | 0.102 | 0.097 | 0.094 | 0.090 | 0.082 |
| +Ex. 1 | 0.60 | 0.091 | 0.098 | 0.098 | 0.090 | 0.083 | 0.084 |
| +Ex. 2 | 0.60 | 0.084 | 0.098 | 0.105 | 0.104 | 0.099 | 0.091 |
| +Ex. 5 | 0.60 | 0.097 | 0.106 | 0.109 | 0.104 | 0.098 | 0.092 |
| +CEx. 1 | 1.00 | 0.079 | 0.083 | 0.082 | 0.077 | 0.075 | 0.071 |
| +CEx. 2 | 1.00 | 0.086 | 0.093 | 0.098 | 0.093 | 0.081 | 0.085 |
| +Ex. 1 | 1.00 | 0.087 | 0.094 | 0.096 | 0.086 | 0.077 | 0.069 |
| +Ex. 2 | 1.00 | 0.089 | 0.095 | 0.103 | 0.098 | 0.094 | 0.092 |
| +Ex. 5 | 1.00 | 0.092 | 0.101 | 0.103 | 0.100 | 0.094 | 0.086 |

*Reported coefficients are the average of three runs. Boundary coefficient is the coefficient of friction at a speed of 10 mm/s.

TABLE 6

Tribological Performance Testing by MTM at Additional Treat Rates

| Additive | FM Treat Rate (wt. %) | Stribeck Coefficient* at Specified Temperature | | | | | |
|---|---|---|---|---|---|---|---|
| | | 40° C. | 60° C. | 80° C. | 100° C. | 120° C. | 140° C. |
| 0W-20 PCMO | 0 | 0.135 | 0.141 | 0.167 | 0.219 | 0.268 | 0.278 |
| +CEx. 1 | 0.40 | 0.135 | 0.138 | 0.146 | 0.155 | 0.159 | 0.148 |
| +CEx. 2 | 0.40 | 0.142 | 0.149 | 0.157 | 0.162 | 0.170 | 0.202 |
| +Ex. 1 | 0.40 | 0.139 | 0.143 | 0.154 | 0.161 | 0.168 | 0.177 |
| +Ex. 2 | 0.40 | 0.146 | 0.148 | 0.157 | 0.166 | 0.181 | 0.195 |
| +Ex. 5 | 0.40 | 0.145 | 0.151 | 0.167 | 0.181 | 0.195 | 0.201 |
| +CEx. 1 | 0.60 | 0.129 | 0.126 | 0.130 | 0.137 | 0.143 | 0.139 |
| +CEx. 2 | 0.60 | 0.143 | 0.155 | 0.162 | 0.173 | 0.185 | 0.180 |
| +Ex. 1 | 0.60 | 0.148 | 0.143 | 0.144 | 0.144 | 0.146 | 0.153 |
| +Ex. 2 | 0.60 | 0.143 | 0.143 | 0.155 | 0.165 | 0.178 | 0.191 |
| +Ex. 5 | 0.60 | 0.154 | 0.154 | 0.157 | 0.160 | 0.169 | 0.184 |
| +CEx. 1 | 1.00 | 0.132 | 0.129 | 0.135 | 0.141 | 0.150 | 0.145 |
| +CEx. 2 | 1.00 | 0.133 | 0.132 | 0.137 | 0.144 | 0.139 | 0.148 |
| +Ex. 1 | 1.00 | 0.145 | 0.137 | 0.137 | 0.129 | 0.122 | 0.118 |
| +Ex. 2 | 1.00 | 0.145 | 0.142 | 0.149 | 0.163 | 0.168 | 0.186 |
| +Ex. 5 | 1.00 | 0.147 | 0.143 | 0.142 | 0.142 | 0.144 | 0.153 |

*Stribeck coefficients are calculated by taking the integration of the Stribeck curve at each individual temperature.

Example 9

Copper and Lead Corrosion Testing by High Temperature Corrosion Bench Test (HTCBT)

The test method described for ASTM D6594 (Standard Test Method for Evaluation of Corrosiveness of Diesel Engine Oil at 135° C.) was followed to generate the copper and lead corrosion data contained in Table 7. For API CK-4 category and equivalent oils, the limits for passing the HTCBT are 20 ppm maximum for copper, 120 ppm maximum for lead, and a 3 maximum copper rating. From the data presented in Table 7, the inventive examples provide significant improvements over the comparative examples with respect the copper and lead corrosion. The data clearly indicate that the inclusion of CEx. 1 as an FM additive in the 15W-40 HDDEO results in a significant amount of both copper and lead corrosion. The formulation containing CEx. 1, which is a purely ester-based additive, fails for copper corrosion and severely fails for lead corrosion. Alternatively, CEx. 2 is a mixture of both amide- and ester-based compounds. For CEx. 2, the oil now passes for copper corrosion. While the oil containing CEx. 2 still results in a severe failure for lead corrosion, the observed lead values have been reduced over 70%. The inventive examples are purely amide-based materials. For Ex. 1, the formulation passes for copper and is a borderline fail for lead corrosion. However, formulations containing either inventive Ex. 2 or Ex. 5 pass for both copper and lead corrosion and also match the copper rating for the reference 15W-40 HDDEO. Inventive Ex. 2 and Ex. 5 compared to CEx. 1 represent a 75% reduction in the copper corrosion and nearly a 90% reduction in the lead corrosion. In addition, inventive Ex. 2 and Ex. 5 benefit from more than a 60% reduction in the lead corrosion compared to CEx. 2.

TABLE 7

Copper and Lead Corrosion Testing by HTCBT (ASTM D6594)

| Additive | FM Treat Rate (wt. %) | Cu (ppm)* | Cu Rating | Pb (ppm)* |
|---|---|---|---|---|
| 15W-40 HDDEO | 0 | 6.0 | 1b | 7.5 |
| +CEx. 1 | 0.75 | 40.0 | 2e | 925.0 |
| +CEx. 2 | 0.75 | 6.0 | 1b | 270.0 |
| +Ex. 1 | 0.75 | 14.5 | 1b | 145.0 |
| +Ex. 2 | 0.75 | 10.0 | 1b | 103.5 |
| +Ex. 5 | 0.75 | 11.0 | 1b | 103.0 |

*Average of at least two runs

The results of the frictional performance, wear protection, and corrosion testing demonstrate that the inventive examples represent a new class of additives capable of meeting or exceeding the frictional and wear performance of traditional additives while significantly reducing the severity of the observed copper and lead corrosion.

What is claimed is:

1. A lubricating composition comprising at least 80% of a lubricating base oil and 0.01-5 weight % of an additive compound represented by the following formula:

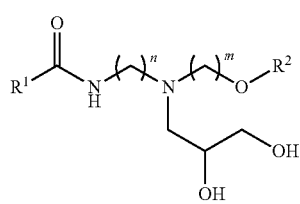

where R1 is an unsaturated or branched hydrocarbon chain, R2 is either a hydrogen atom or a hydrocarbon chain, and m and n are independently from 1 to 5.

2. The lubricating composition of claim 1, wherein the additive compound is the reaction product of (a) a carboxylic acid or ester;

(b) one of (i) 2-aminoethylethanolamine, (ii) alkyloxypropyl-1,3-diaminopropane (iii) alkyloxyethyl-1,3-diaminopropane, and (iv) alkyloxypropyl-1,2-diaminoethane; and (c) glycidol.

3. The lubricating composition of claim 1, wherein the additive compound is present at about 0.20-2.00%.

4. The lubricating composition of claim 1, wherein the additive compound is chosen from the group consisting of:

N-[2-[(2,3-dihydroxypropyl)(2-hydroxyethyl)amino]ethyl]alkaneamide;

N-[2-[(2,3-dihydroxypropyl)(2-hydroxyethyl)amino]ethyl]isostearamide;

N-[2-[(2,3-dihydroxypropyl)(2-hydroxyethyl)amino]ethyl]oleamide;

N-[3-[(2,3-dihydroxypropyl)(3-alkyloxypropyl)amino]propyl]alkaneamide;

N-[3-[(2,3-dihydroxypropyl)(3-alkyloxypropyl)amino]propyl]isostearamide; and

N-[3-[(2,3-dihydroxypropyl)(3-alkyloxypropyl)amino]propyl]oleamide.

5. A lubricating composition comprising at least 80% of a lubricating base oil and 0.01-5 weight % of an additive being a mixture of compounds represented by the following formula:

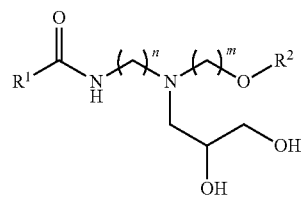

wherein said mixture comprises at least one first compound having a hydrocarbon chain which is unsaturated or branched, and at least one second compound having a hydrocarbon chain which is saturated and unbranched; and where R2 is either a hydrogen atom or a hydrocarbon chain, and m and n are independently from 1 to 5.

6. The lubricating composition of claim 5, wherein the additive is the reaction product of (a) a carboxylic acid or ester;

(b) one of (i) 2-aminoethylethanolamine, (ii) alkyloxypropyl-1,3-diaminopropane (iii) alkyloxyethyl-1,3-diaminopropane, and (iv) alkyloxypropyl-1,2-diaminoethane; and (c) glycidol.

7. The lubricating composition of claim 5, wherein the additive is present at about 0.20-2.00 weight %.

8. The lubricating composition of claim 5, wherein the additive is chosen from the group consisting of:

N-[2-[(2,3-dihydroxypropyl)(2-hydroxyethyl)amino]ethyl]cocoamide; and

N-[3-[(2,3-dihydroxypropyl)(3-alkyloxypropyl)amino]propyl]cocoamide.

* * * * *